(12) United States Patent
Sobol et al.

(10) Patent No.: US 12,295,960 B2
(45) Date of Patent: May 13, 2025

(54) CANCER TREATMENT (71) Applicants: University of South Alabama Foundation for Research and Commercialization, Mobile, AL (US); Canal House Biosciences, LLC, Providence, RI (US)

(72) Inventors: Robert W. Sobol, Providence, RI (US); Jay George, Gaithersburg, MD (US)

(73) Assignees: UNIVERSITY OF SOUTH ALABAMA FOUNDATION FOR RESEARCH AND COMMERCIALIZATION, Mobile, AL (US); CANAL HOUSE BIOSCIENCES, LLC, Providence, RI (US)

( * ) Notice: Subject to any disclaimer, the term of this patent is extended or adjusted under 35 U.S.C. 154(b) by 0 days.

(21) Appl. No.: 18/571,452

(22) PCT Filed: Oct. 17, 2022

(86) PCT No.: PCT/US2022/046832
§ 371 (c)(1),
(2) Date: Dec. 18, 2023

(87) PCT Pub. No.: WO2023/064619
PCT Pub. Date: Apr. 20, 2023

(65) Prior Publication Data
US 2024/0285647 A1   Aug. 29, 2024

Related U.S. Application Data

(60) Provisional application No. 63/256,595, filed on Oct. 17, 2021.

(51) Int. Cl.
| | | |
|---|---|---|
| *A61K 31/5517* | (2006.01) | |
| *A61K 31/145* | (2006.01) | |
| *A61K 31/4045* | (2006.01) | |
| *A61K 31/454* | (2006.01) | |
| *A61K 31/501* | (2006.01) | |
| *A61K 31/502* | (2006.01) | |
| *A61K 31/517* | (2006.01) | |
| *A61K 31/5377* | (2006.01) | |
| *A61K 45/06* | (2006.01) | |
| *A61P 35/00* | (2006.01) | |
| *G01N 33/68* | (2006.01) | |

(52) U.S. Cl.
CPC ........ *A61K 31/5517* (2013.01); *A61K 31/145* (2013.01); *A61K 31/4045* (2013.01); *A61K 31/454* (2013.01); *A61K 31/501* (2013.01); *A61K 31/502* (2013.01); *A61K 31/517* (2013.01); *A61K 31/5377* (2013.01); *A61K 45/06* (2013.01); *A61P 35/00* (2018.01); *G01N 33/6893* (2013.01); *G01N 2333/4703* (2013.01)

(58) Field of Classification Search
CPC .............. A61K 31/5517; A61K 31/145; A61K 31/4045; A61K 31/454; A61K 31/501; A61K 31/502; A61K 31/517; A61K 31/5377; A61K 45/06; A61K 31/4184; A61K 31/455; A61K 31/5025; A61K 31/55; A61K 31/706; A61K 31/7084; A61P 35/00; G01N 33/6893; G01N 2333/4703
See application file for complete search history.

(56) References Cited

U.S. PATENT DOCUMENTS

| | | | |
|---|---|---|---|
| 5,166,140 A | * | 11/1992 | Scanlon ................. A61K 31/70 514/45 |
| 6,339,073 B1 | | 1/2002 | Pero |
| 8,143,241 B2 | | 3/2012 | Ashworth et al. |
| 8,197,807 B2 | | 6/2012 | Brenner |
| 8,383,086 B2 | | 2/2013 | Brenner |
| 10,995,073 B2 | | 5/2021 | McGonagle et al. |
| 2012/0135983 A1 | | 5/2012 | Ashworth et al. |
| 2019/0350960 A1 | * | 11/2019 | Sinclair ............. A61K 31/7084 |
| 2020/0306229 A1 | | 10/2020 | Castro et al. |
| 2021/0106574 A1 | | 4/2021 | Feng et al. |

FOREIGN PATENT DOCUMENTS

| | | | | |
|---|---|---|---|---|
| WO | 2015051766 A1 | | 4/2015 | |
| WO | WO-2018129039 A1 | * | 7/2018 | |
| WO | WO-2018237296 A1 | * | 12/2018 | .............. A61P 35/00 |
| WO | 2020023802 A1 | | 1/2020 | |
| WO | WO-2021180741 A1 | * | 9/2021 | ............. A23L 33/10 |
| WO | 2021262898 A1 | | 12/2021 | |

OTHER PUBLICATIONS

Jain et al. Poly (ADP) ribose glycohydrolase can be effectively targeted in pancreatic cancer (Cancer Res. 79(17): 1-21). (Year: 2019).*
Zhang et al. Nicotinamide prohibits proliferation and enhances chemosensitivity of pancreatic cancer cells through deregulating SIRT1 and Ras/Akt pathways (Pancreatology, 13, 140-146). (Year: 2013).*
Ditano, Sensitivity of cells to ATR and CHK1 inhibitors requires hyperactivation of CDK2 rather than endogenous replication stress or ATM dysfunction, Nature Portfolio (2021)11:7077.
Gravells, Specific killing of DNA damage-response deficient cells with inhibitors of poly(ADP-ribose) glycohydrolase, DNA Repair 52 (2017) 81-91 Elsevier B.V.
Ha, Antitumor effect of a WEE1 inhibitor and potentiation of olaparib sensitivity by DNA damage response modulation in triple-negative breast cancer, Nature Research Scientific Reports (2020) 10:9930.

(Continued)

*Primary Examiner* — Joseph K McKane
*Assistant Examiner* — Meghan C Heasley
(74) *Attorney, Agent, or Firm* — Karta Law; Glenn E. Karta (57) ABSTRACT

The present invention relates to methods for the treatment of cancers, as well as pharmaceutical preparations of compounds useful in such treatments.

5 Claims, 4 Drawing Sheets (56) References Cited

OTHER PUBLICATIONS

Houl, Selective small molecule PARG inhibitor causes replication fork stalling and cancer cell death, Nature Communications (2019) 10:5654.
Italiano, ATR inhibition as an attractive therapeutic resource against cancer, Cancer Discovery 2021; 11; 14-6.
Jin, ATM in DNA repair in cancer, Pharmacology & Therapeutics 203 (2019)107391 Elsevier.
Lavin, Clinical potential of ATM inhibitors, Mutat Res Fund Mol Mech Mutagen 821 (2020) 111695 Elsevier.
Rose, PARP inhibitors: clinical relevance, mechanisms of action and tumor resistance, Front. Cell Dev. Biol. 8:564601 (2020).
Xu, CHK2 inhibition provides a strategy to suppress hematologic toxicity from PARP inhibitors, Mol Cancer Res 2021, 19:1350-60.
Zatreanu, Pol inhibitors elicit BRCA-gene synthetic lethality and target PARP inhibitor resistance, Nature Communications (2021) 12:3636.
Zhou, A first-in-class polymerase theta inhibitor selectively targets homologous-recombination-deficient tumors, Nature Cancer, vol. 2, Jun. 2021, 598-610.

\* cited by examiner

CANCER TREATMENT

CROSS REFERENCE TO RELATED APPLICATIONS

This application claims the benefit of the filing date of U.S. application Ser. No. 63/256,595, filed Oct. 17, 2021, the disclosure of which is incorporated herein by reference in its entirety.

STATEMENT REGARDING FEDERALLY SPONSORED RESEARCH OR DEVELOPMENT

This invention was made with government support under NIH-NCI/R01CA148629 and NIH-NCI/1R01CA238061 awarded by the Department of Health and Human Services/National Institutes of Health/National Cancer Institute. The government has certain rights in the invention.

BACKGROUND OF THE INVENTION

1. Field of the Invention

The present invention relates to methods for the treatment of cancers, as well as pharmaceutical preparations of compounds useful in such treatments.

SUMMARY OF THE INVENTION

In one aspect, the present invention relates to a method for the treatment of a cancer, which comprises administering to a subject in need of such treatment:
  a) a pharmaceutically effective amount of a compound that increases the amount of $NAD^+$ in the subject's cancer cells, and
  b) a pharmaceutically effective amount of one or more of i) a PARG inhibitor, ii) a PARP1 inhibitor, or iii) a PARP2 inhibitor.

In some embodiments, the compounds are administered in any order or simultaneously.

In some embodiments, the compound that increases the amount of $NAD^+$ comprises one or more of nicotinamide adenine dinucleotide ($NAD^+$), nicotinic acid (NA), nicotinamide riboside (NR), nicotinamide (NAM), nicotinic acid adenine dinucleotide (NAAD), nicotinamide mononucleotide (NMN), nicotinic acid mononucleotide (NaMN), nicotinic acid ribonucleoside (NAR), inositol hexanicosinate (INH) or dihydronicotinamide riboside (NRH).

In some embodiments, the PARG inhibitor comprises one or more of (E)-1-(((p-Tolylthio)imino)methyl)naphthalen-2-ol; 1,3,6,9-Tetrahydro-1,3-dimethyl-8-[[2-(4-morpholinyl)ethyl]thio]-6-thioxo-2H-purin-2-one; and 1-[(1,3-Dimethyl-1H-pyrazol-5-yl)methyl]-1,2,3,4-tetrahydro-N-(1-methylcyclopropyl)-3-[(2-methyl-5-thiazolyl)methyl]-2,4-dioxo-6-quinazolinesulfonamide.

In some embodiments, the PARP1 or PARP2 inhibitor comprises one or more of Olaparib, Rucaparib, Niraparib, Talazoparib, or Veliparib.

In some embodiments, the cancer cells contain a functional MSH6 protein.

In some embodiments, the cancer is selected from a carcinoma, a sarcoma, a leukemia, a lymphoma, or a myeloma.

In some embodiments, the tumor comprises a glioma.

In some embodiments, the method further comprises determining whether the cancer to be treated contains a functional MSH6 protein prior to administering the compounds.

In yet another aspect, the present invention relates to a pharmaceutical composition which comprises:
  a) a pharmaceutically effective amount of a compound that increases the amount of $NAD^+$ in the cells of a subject to whom the composition is administered;
  b) a pharmaceutically effective amount of one or more of i) a PARG inhibitor, ii) a PARP1 inhibitor, or iii) a PARP2 inhibitor; and
  c) optionally a pharmaceutically acceptable carrier.

In some embodiments, the composition is injectable.

In some embodiments, the composition is in the form of nanoparticles.

In another aspect, the present invention relates to a method for the treatment of a cancer, which comprises administering to a subject in need of such treatment:
  a) a pharmaceutically effective amount of a compound that inhibits DNA repair; and
  b) a pharmaceutically effective amount of one or more of i) a PARP1 inhibitor, ii) a PARP2 inhibitor, or iii) a PARG inhibitor; and
  c) optionally a pharmaceutically effective amount of a compound that increases the amount of $NAD^+$ in the subject's cancer cells.

In some embodiments, the compound that increases the amount of NAD comprises one or more of nicotinamide adenine dinucleotide ($NAD^+$), nicotinic acid (NA), nicotinamide riboside (NR), nicotinamide (NAM), nicotinic acid adenine dinucleotide (NAAD), nicotinamide mononucleotide (NMN), nicotinic acid mononucleotide (NaMN), nicotinic acid ribonucleoside (NAR), inositol hexanicosinate (INH) or dihydronicotinamide riboside (NRH).

In some embodiments, the PARG inhibitor comprises one or more of (E)-1-(((p-Tolylthio)imino)methyl)naphthalen-2-ol; 1,3,6,9-Tetrahydro-1,3-dimethyl-8-[[2-(4-morpholinyl)ethyl]thio]-6-thioxo-2H-purin-2-one; and 1-[(1,3-Dimethyl-1H-pyrazol-5-yl)methyl]-1,2,3,4-tetrahydro-N-(1-methylcyclopropyl)-3-[(2-methyl-5-thiazolyl)methyl]-2,4-dioxo-6-quinazolinesulfonamide.

In some embodiments, the PARP1 or PARP2 inhibitor comprises one or more of Olaparib, Rucaparib, Niraparib, Talazoparib, or Veliparib.

In other embodiments, the invention relates to a kit comprising i) one or more of the pharmaceutical compositions described herein; ii) suitable packaging material; and iii) instructions for use of the composition

DETAILED DESCRIPTION OF THE INVENTION

It has now been discovered that tumor cell growth may be reduced or eliminated by administering to the cells the combination of a pharmaceutically effective amount of a) compound that increases the amount of $NAD^+$ in the tumor cells, and b) a pharmaceutically effective amount of a PARG inhibitor and/or a pharmaceutically effective amount of a compound that inhibits PARP1 and/or PARP2. Further, it has been discovered that tumor cell growth may be reduced or eliminated by administering to the cells a) a pharmaceutically effective amount of a compound that inhibits DNA repair; and b) a pharmaceutically effective amount of one or more of i) a PARP1 inhibitor, ii) a PARP2 inhibitor, or iii) a PARG inhibitor; and c) optionally a pharmaceutically effective amount of a compound that increases the amount of NAD⁺ in the subject's cancer cells.

Figure 1A:
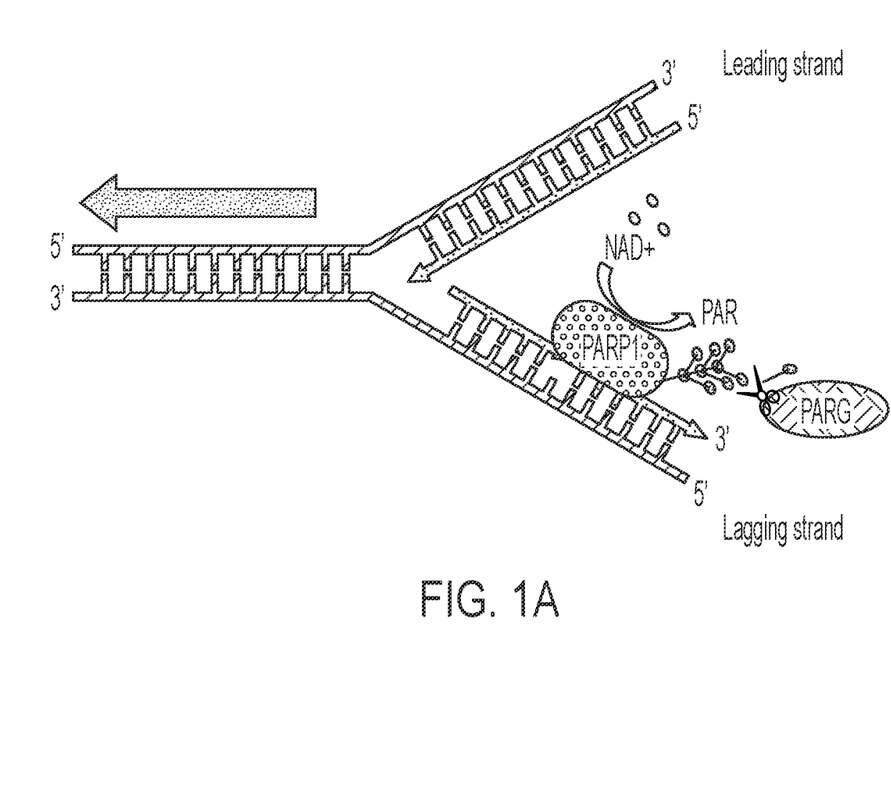
FIGS. 1A, 1B, and 1C depict a possible mechanism of the present invention.
Figure 1B:
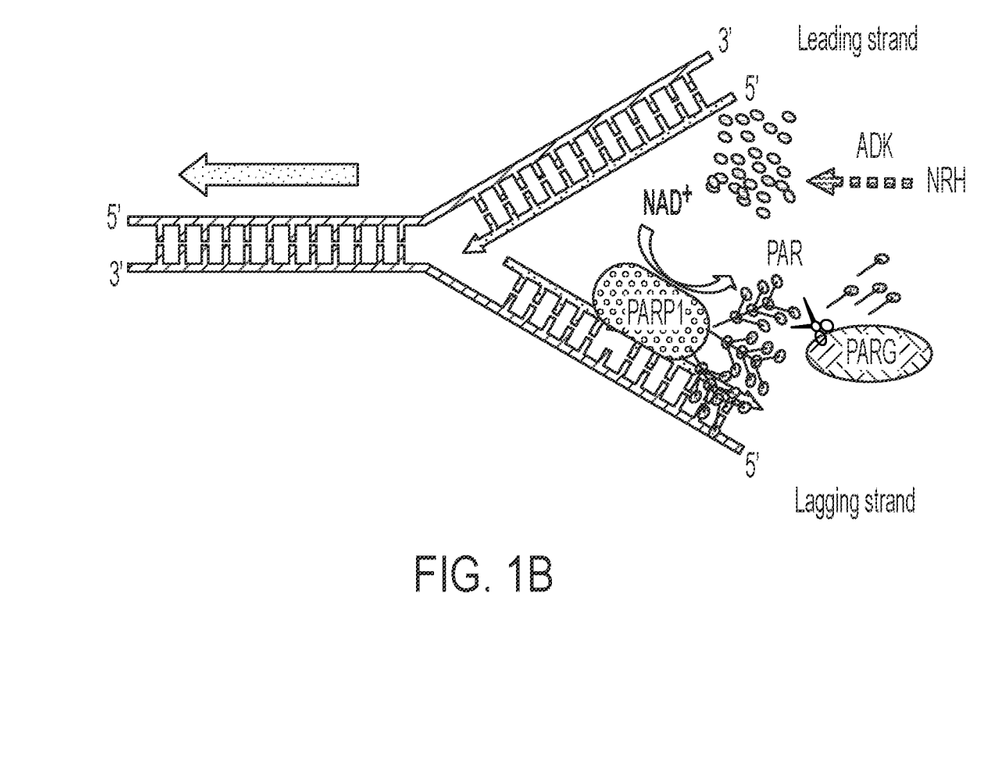
Figure 1C:
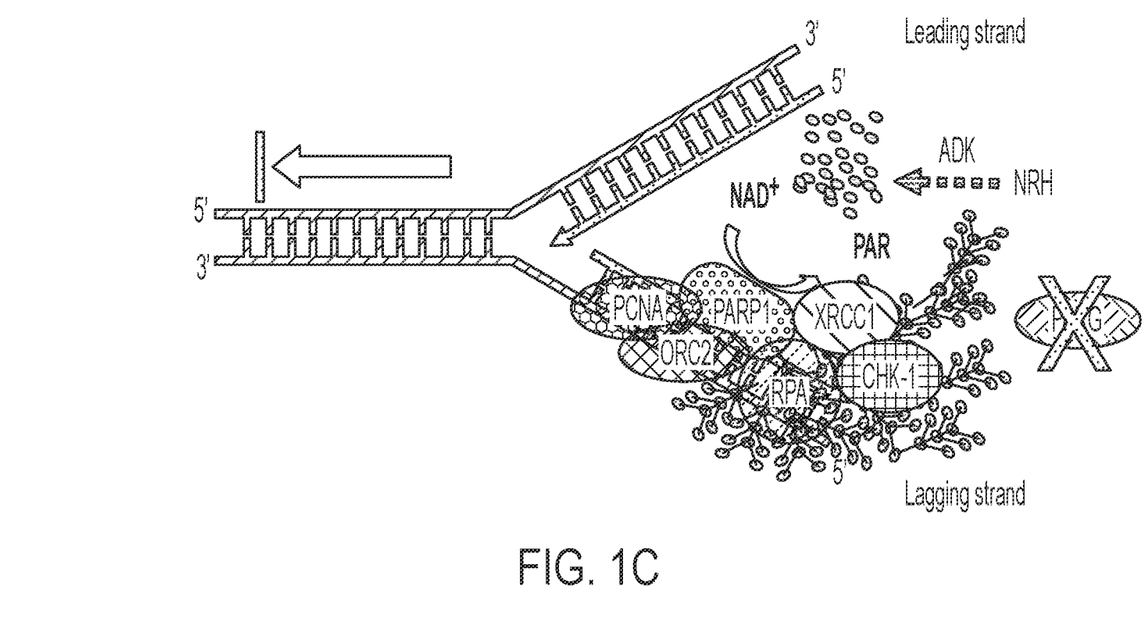

Without wishing to be bound by any particular theory of operation, following is a model of replication-associated PARP1 activation, defining PARGi-induced replication arrest and dependence on NRH-enhanced levels of cellular NAD⁺. FIGS. 1A, 1B, and 1C depict a hypothetical binding site for PARP1 on the lagging strand, post-replication, likely associated with Okazaki-fragment processing (although the PARP1 binding site is not defined):

FIG. 1A: A low NAD⁺/PARP1 ratio can suppress PARP1 activation potential, allowing robust DNA replication with minimal PAR accumulation.

FIG. 1B: Alteration of the NAD/PARP1 ratio by NRH delivery promotes elevated replication associated PARP1 activation and a suppression of replication fork progression.

FIG. 1C: Combination of (i) NRH to enhance cellular NAD⁺ levels and (ii) PARG inhibition, leads to rapid accumulation of PAR resulting from replication associated PARP1 activation. PAR accumulation at the replication fork leads to complexation of PARP1 with BER/SSBR proteins such as XRCC1 and replication proteins including RPA, PCNA and ORC2, triggering the onset of CHK1 phosphorylation, an intra S-phase checkpoint and the onset of apoptosis.

Compounds that increase the amount of NAD⁺ (nicotinamide adenine dinucleotide) in cells are well known. Such compounds include, in addition to NAD⁺ itself, one or more of various NAD⁺ precursors such as nicotinic acid (NA), nicotinamide riboside (NR), nicotinamide (NAM), nicotinic acid adenine dinucleotide (NAAD), nicotinamide mononucleotide (NMN), nicotinic acid mononucleotide (NaMN), nicotinic acid ribonucleoside (NAR), inositol hexanicosinate (INH) or dihydronicotinamide riboside (NRH).

PARG inhibitors are also known. PARG (Poly (ADP-ribose) Glycohydrolase) is the major enzyme responsible for the catabolism of poly (ADP-ribose), a reversible covalent-modifier of chromosomal proteins. The protein is found in many tissues and may be subject to proteolysis generating smaller, active products. Known PARG inhibitors include (E)-1-(((p-Tolylthio)imino)methyl)naphthalen-2-ol (CAS: 906439-72-3; COH34); 1,3,6,9-Tetrahydro-1,3-dimethyl-8-[[2-(4-morpholinyl)ethyl]thio]-6-thioxo-2H-purin-2-one (CAS 6505-99-3; JA2131); 1-[(1,3-Dimethyl-1H-pyrazol-5-yl)methyl]-1,2,3,4-tetrahydro-N-(1-methylcyclopropyl)-3-[(2-methyl-5-thiazolyl)methyl]-2,4-dioxo-6-quinazolinesulfonamide (CAS 1945950-21-9; PDD00017273); etc.

PARP1 and/or PARP2 inhibitors are also known. PARP (Poly (ADP-ribose) polymerase) is a family of proteins involved in a number of cellular processes such as DNA repair, genomic stability, and programmed cell death. Known PARP1 and PARP2 inhibitors include compounds such as Olaparib, Rucaparib, Niraparib, Talazoparib, Veliparib, etc. These compounds may bind in the NAD binding site.

DNA repair inhibitors are also known to one of ordinary skill. For example, a non-exhaustive list of such inhibitors, also listing the proteins inhibited, and representative publication references, follows (the list of references is found at the end of this disclosure, the disclosures of which are hereby incorporated by reference):

KU-55933, KU-60019, KU-59403, CP-466722, AZ31, AZ32, AZD0156, and AZD1390 which inhibit ATM (Refs. (6) and (7)).

M6620, AZD6738, and BAY1895344 which inhibit ATR (Ref. (5)).

MK-8776 and AZD7762 which inhibit CHK1 (Ref. (1)).

BML-277 and AZD7762 which inhibit CHK2 (Ref. (9)).

Olaparib, Rucaparib, Niraparib, and Talazoparib which inhibit PARP1/PARP2 (Ref. (8)).

PDD00017273 and JA2131 which inhibit PARG (Refs. (2) and (4)).

AZD1775 which inhibits Wee1 (Ref. (3)).

ART558 and Novobiocin which inhibit polymerase theta (Refs. (10) and (11)).

The present invention may be used to treat potentially any tumor, for example carcinomas, sarcomas, leukemias, lymphomas, myelomas, etc. In a preferred embodiment, the tumor is one undergoing replication stress. In another preferred embodiment, the tumor contains a functional MSH-6 protein. In yet another preferred embodiment, the tumor is a glioma.

In another preferred embodiment, prior to treatment, the tumor is analyzed to determine whether it contains a functional MSH6 protein. The various methods of analysis would be known to one of ordinary skill and include immunohistochemistry, immunocytochemistry and/or DNA sequencing. In this embodiment, tumors testing negative for MSH6 would not be candidates for the treatment described above.

The administration of the compounds described herein may take place by co-administering the active components or agents, such as, e.g., by administering them simultaneously or concurrently in one single or in multiple separate formulations or dosage forms. Alternatively, the administration of the compounds described herein may take place by administering the active components or agents sequentially or in alteration, such as, e.g., in multiple separate formulations or dosage forms.

For example, simultaneous administration includes administration at substantially the same time. This form of administration may also be referred to as "concomitant" administration. Concurrent administration includes administering the active agents within the same general time period, for example on the same day(s) but not necessarily at the same time. Alternate administration includes administration of one agent during a time period, for example over the course of a few days or a week, followed by administration of the other agent(s) during a subsequent period of time, for example over the course of a few days or a week, and then repeating the pattern for one or more cycles. Sequential or successive administration includes administration of one agent during a first time period (for example over the course of a few days or a week) using one or more doses, followed by administration of the other agent(s) during a second time period (for example over the course of a few days or a week) using one or more doses. An overlapping schedule may also be employed, which includes administration of the active agents on different days over the treatment period, not necessarily according to a regular sequence. Variations on these general guidelines may also be employed, e.g., according to the agents used and the condition of the subject.

For purposes of the following detailed description, the following shorthand designations may be used:

Compound A—the one or more compounds that increase the amount of NAD⁺ in the subject's cancer cells.

Compound B—the one or more PARG inhibitors.

Compound C—the one or more PARP inhibitors (PARP1 and/or PARP2).

Compound D—the one or more compounds that inhibit DNA repair.

Accordingly, in a preferred embodiment, in the methods according the present invention, Compound A as described herein is administered simultaneously, concurrently, sequentially, successively, alternately or separately with Compounds B, C, and/or D as described herein. In a related preferred embodiment, Compound B, as described herein for use in a method according to the present invention, is administered simultaneously, concurrently, sequentially, successively, alternately or separately with Compounds A, C, and/or D as described herein. In another embodiment, the kit according to the present invention is provided wherein the various compounds A-D are to be administered simultaneously, concurrently, sequentially, successively, alternately or separately.

Preferred routes of administration for any or all of Compound A, Compound B, Compound C and Compound D, administered separately or simultaneously, include, but are not limited to, oral, enteral, parenteral (e.g. intramuscular, intraperitoneal, intravenous, transdermal or subcutaneous injection, or implant), nasal, vaginal, rectal, or topical administration. Topical formulations may include ointments, lotions, creams, gels, drops, suppositories, sprays, liquids and powders. Oral formulations include powders, granules, suspensions or solutions in water or non-aqueous media, capsules or tablets, for example. Thickeners, flavorings, diluents, emulsifiers, dispersing aids or binders may be used as needed. Parenteral formulations may include sterile aqueous solutions which may also contain buffers, diluents and other suitable additives. In a preferred embodiment, the parenteral formulation may be in the form of nanoparticles. In a preferred embodiment, the route of administration is intravenous administration, especially intravenous infusion or injection. The compounds of the present invention may be formulated, alone or together, in suitable dosage unit formulations containing conventional non-toxic pharmaceutically acceptable carriers, excipients and/or vehicles appropriate for each route of administration. More preferably, formulations include solid, semi-solid or liquid dosage forms, such as lyophilisation, liquid solutions (e.g. injectable and infusible solutions), dispersions or suspensions, liposomes and suppositories. The preferred mode depends on the intended mode of administration and therapeutic application. Especially preferred embodiments include liquid formulations and lyophilisation. In the case of a lyophilisation, the lyophilisate may be reconstituted in a liquid, preferably water.

The compounds as described herein may be administered daily, 5 times a week, 3 times a week, 2 times a week, once a week, once in 2 weeks, once in 3 weeks, once in 4 weeks. Preferable administration intervals include once a week and once in 2 weeks. In a preferred embodiment, any or all of Compounds A, B, C and D are administered once a week by i.v. infusion.

An administration regimen may include long-term treatment. By "long-term" is meant at least two weeks and preferably, several weeks, months or years of duration. Necessary modifications in this dosage regimen may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication. Administration may be daily, every second day, every third day, every fourth day, one day per week, two days per week, one day per two weeks, one day per three weeks, etc.

The compounds as described herein may be administered at therapeutically effective amounts in single or divided doses administered at appropriate time intervals. A therapeutically effective amount refers to an amount effective at dosages and for periods of time necessary to achieve the desired therapeutic result and is the minimum amount necessary to prevent, ameliorate, or treat a disease or disorder. A therapeutically effective amount of the compounds according to the present invention may vary according to factors such as the disease state, age, sex, and weight of the individual, and the ability of the compound to elicit a desired response in the individual. A therapeutically effective amount is also one in which any toxic or detrimental effects of the compound is outweighed by the therapeutically beneficial effects. A therapeutically effective dose preferably inhibits a measurable parameter, e.g. a tumor growth rate by at least about 20%, more preferably by at least about 40%, even more preferably by at least about 60%, and still more preferably by at least about 80% relative to untreated subjects or relative to a preceding untreated period of the same subject that is to be treated.

The active compounds may be administered in such doses which are therapeutically effective in monotherapy, or in such doses which are lower or higher than the doses used in monotherapy, but when combined result in a desired (jointly) therapeutically effective amount.

The desired dose of each of the compounds used in the present invention may be administered as a fixed amount per administration or as bolus, to reach a set blood concentration in the patient.

Administration of the compounds described herein may, e.g., be by injection (e.g. subcutaneously or intravenously) at a dose of about 0.1 to 30 mg/kg of patient body weight, about 0.5 to 25 mg/kg of patient body weight, about 1 to 20 mg/kg of patient body weight, about 2 to 5 mg/kg of patient body weight, or about 3 mg/kg of patient body weight.

Dosages and therapeutic regimens of the compounds can be determined by a skilled artisan. Preferred dosage regimens for the compounds of the invention include 1 mg/kg of host body weight or 3 mg/kg of host body weight via intravenous administration, with the compound being given using one of the following dosing schedules: (i) every four weeks for six dosages, then every three months; (ii) every three weeks; (iii) 3 mg/kg of host body weight once followed by 1 mg/kg of host body weight every three weeks. In certain embodiments, the compounds may be administered by injection (e.g., subcutaneously or intravenously) at a dose of about 1 to 40 mg/kg of host body weight, e.g., 1 to 30 mg/kg of host body weight, e.g., about 5 to 25 mg/kg of host body weight, about 10 to 20 mg/kg of host body weight, about 1 to 5 mg/kg of host body weight, 1 to 10 mg/kg of host body weight, 5 to 15 mg/kg of host body weight, 10 to 20 mg/kg of host body weight, 15 to 25 mg/kg of host body weight, or about 3 mg/kg of host body weight. The dosing schedule can vary from e.g., once a week to once every 2, 3, or 4 weeks. In one embodiment, the compounds may be administered at a dose from about 10 to 20 mg/kg of host body weight every other week. The compounds may be administered by intravenous infusion at a rate of more than 20 mg/min, e.g., 20-40 mg/min, and typically greater than or equal to 40 mg/min to reach a dose of about 35 to 440 mg/m$^2$, typically about 70 to 310 mg/m$^2$, and more typically, about 110 to 130 mg/m$^2$. In embodiments, the infusion rate of about 110 to 130 mg/m$^2$ achieves a level of about 3 mg/kg of host body weight. In other embodiments, the present compounds may be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, or, about 10 mg/m$^2$. In some embodiments, the compounds may be infused over a period of about 30 min. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The dosing schedule of the compounds described herein, separately or together, may vary from e.g. once a week to once every 2, 3 or 4 weeks. In a certain embodiment, the administered amount or dosage of each individual or combination of compounds is lower (e.g. at least 20%, at least 30%, at least 40%, or at least 50% lower). In other embodiments, the amount or dosage of each individual or combination of compounds that results in a desired effect (e.g. treatment of a hyperproliferative or oncological disease) is lower (e.g. at least 20%, at least 30%, at least 40%, or at least 50% lower).

The method, compounds, compounds for use, uses of compounds, pharmaceutical composition and kit according to the present invention comprises administering to the subject a combination of the compounds as described herein.

Depending on the cancerous disease to be treated, the combination therapy as defined herein may be used on its own or in further combination with one or more additional therapeutic modalities, in particular selected from radiation, chemotherapeutic agents or therapeutically active compounds that inhibit Okazaki fragment processing, angiogenesis, signal transduction pathways or mitotic checkpoints in cancer cells or may introduce unusual nucleotides during replication to increase replication stress, such as gemcitabine and related nucleotide or nucleoside analogs.

The additional therapeutic agent may be administered simultaneously with, optionally as a component of the same pharmaceutical preparation, or before or after administration of the compounds described herein.

As outlined above, the present invention relates to a pharmaceutical composition comprising one or more of Compounds A-D as defined herein, and also to a kit comprising a one or more of Compounds A-D.

The term "pharmaceutical composition" as defined herein refers to a preparation which is in such form as to permit the biological activity of an active ingredient contained therein to be effective, and which contains no additional components which are unacceptably toxic to a subject to which the composition would be administered. A pharmaceutical composition of the present invention can be administered by a variety of methods known in the art. As will be appreciated by the skilled artisan, the route and/or mode of administration will vary depending upon the desired results.

Regardless of the route of administration selected, the compounds described herein may be formulated into pharmaceutically acceptable dosage forms by conventional methods known to those of skill in the art.

The kit as defined herein may comprise a suitable container or several suitable containers comprising the one or more of the compounds described herein, in the same container or in different containers. The kit may be used in any method or any uses of the invention.

Preferably, the kit according to the present invention further comprises a package insert comprising readable instructions for using the kit components in the treatment and/or prevention of an oncological or hyperproliferative disease, preferably cancer or a tumor disease, in a patient in need thereof. The instructions may provide further detailes as described above with regard to the inventive method and any of its preferred embodiments.

The compounds within the present methods may be administered to a patient in any order, or simultaneously. The compounds may be formulated in a pharmaceutical composition, which may include, in addition to an effective amount of active ingredients, pharmaceutically acceptable carriers, thickeners, diluents, buffers, preservatives, surface active agents and the like. Pharmaceutical compositions may also include one or more other active ingredients if necessary or desirable.

In general, it is contemplated that unit dosage form compositions according to the present invention will contain from about 0.01 mg to about 500 mg of each active ingredient, preferably about 0.1 mg to about 10 mg of each active ingredient. Topical formulations (such as creams, lotions, solutions, etc.) may have a concentration of each active ingredient of from about 0.1% to about 50%, preferably from about 0.1% to about 10%. However, final strength of the finished dosage form will depend on the factors listed above and may be readily determined by one of ordinary skill, with the goal of reaching maximum increases (for example, a 2-fold increase or greater in a preferred embodiment) in tumor cell levels of NAD$^+$ (resulting from the NRH administration) together with inhibition of PARG.

The use of the word "a" or "an" when used in conjunction with the term "comprising" in the claims and/or the specification may mean "one", but it is also consistent with the meaning of "one or more", "at least one", and "one or more than one".

"About" as used herein means an acceptable degree of error for the quantity measured given the nature of precision of the measurements. Exemplary degrees of error are within 20%, typically within 10%, and more typically within 5% of a given value or range of values.

The term "treating" or "treatment" as used herein means to cure an already present disease state or condition or to increase the likelihood of recovery from the disease state or condition. Treating can also include inhibiting, i.e. arresting the development of a disease state or condition, and ameliorating, i.e. causing regression or delaying progression of a disease. Treatment can be to ameliorate disease symptoms without curing a patient.

The term "preventing" or "prevention" as used herein does not mean to stop a disease state or condition from occurring in a patient or subject completely but may also refer to a reduced risk of developing a disease state or condition.

The present invention is further illustrated by the following examples, without being necessarily limited to these embodiments of the invention. An example or part thereof, including compounds, doses and administration routes, as well as treatment combinations, each as such or in combination with the detailed description above forms part of the invention.

Example 1

Figure 2A:
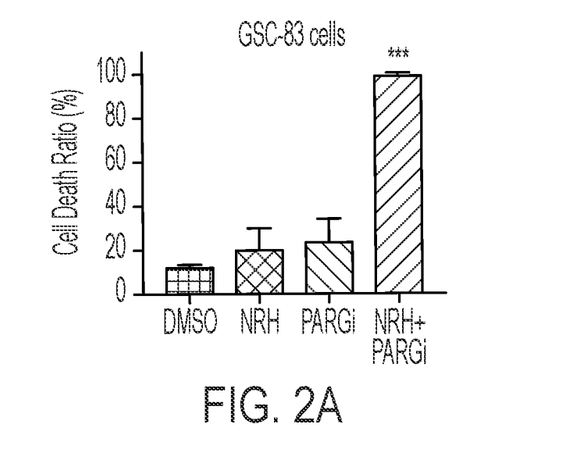
FIGS. 2A, 2B, and 2C show the results of the experiments described in Example 1 below.
Figure 2B:
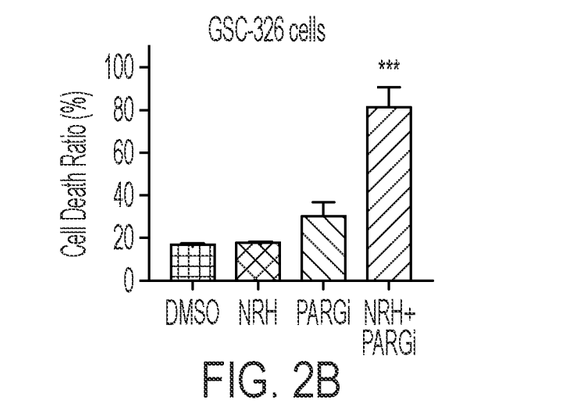
Figure 2C:
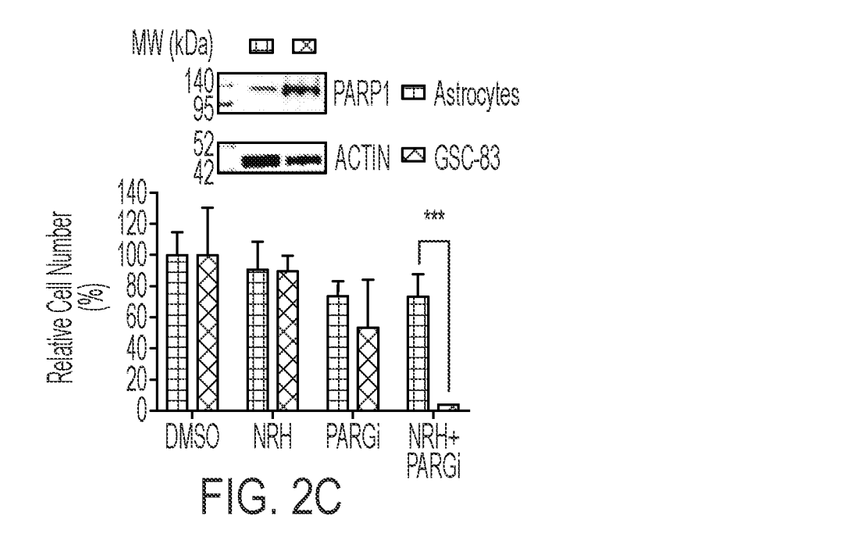

In this example, we established that selective PARGi-induced cell death in glioma stem cells (GSCs) is dependent on NRH-enhanced levels of cellular NAD$^+$. We treated GSC-83 cells, GSC-326 cells, and astrocytes for 5 days with DMSO, NRH (100 µM), PARGi (10 µM) or NRH+PARGi, and evaluated the percentage of dead cells after each treatment. The results are shown in FIGS. 2A and 2B. The treatment with NRH+PARGi resulted in considerably more cell death in GSC-83 cells (FIG. 2A) and GSC-326 cells (FIG. 2B) than with the individual treatments (*p<0.001). FIG. 2C shows the relative number of astrocytes or GSC-83 cells (*p<0.001) remaining after each treatment. The FIG. 2C insert shows an immunoblot analysis of PARP1, comparing astrocytes and GSC-83 cells, with β-Actin used as the loading control.

REFERENCES CITED (1) Ditano, J. P., Donahue, K. L., Tafe, L. J., McCleery, C. F., and Eastman, A. (2021). Sensitivity of cells to ATR and CHK1 inhibitors requires hyperactivation of CDK2 rather than endogenous replication stress or ATM dysfunction. Sci Rep 11, 7077.
(2) Gravells, P., Grant, E., Smith, K. M., James, D. I., and Bryant, H. E. (2017). Specific killing of DNA damage-response deficient cells with inhibitors of poly(ADP-ribose) glycohydrolase. DNA Repair (Amst) 52, 81-91.
(3) Ha, D. H., Min, A., Kim, S., Jang, H., Kim, S. H., Kim, H. J., Ryu, H. S., Ku, J. L., Lee, K. H., and Im, S. A. (2020). Antitumor effect of a WEE1 inhibitor and potentiation of olaparib sensitivity by DNA damage response modulation in triple-negative breast cancer. Sci Rep 10, 9930.
(4) Houl, J. H., Ye, Z., Brosey, C. A., Balapiti-Modarage, L. P. F., Namjoshi, S., Bacolla, A., Laverty, D., Walker, B. L., Pourfarjam, Y., Warden, L. S., et al. (2019). Selective small molecule PARG inhibitor causes replication fork stalling and cancer cell death. Nature communications 10, 5654.
(5) Italiano, A. (2021). ATR Inhibition as an Attractive Therapeutic Resource against Cancer. Cancer discovery 11, 14-16.
(6) Jin, M. H., and Oh, D. Y. (2019). ATM in DNA repair in cancer. Pharmacol Ther 203, 107391.
(7) Lavin, M. F., and Yeo, A. J. (2020). Clinical potential of ATM inhibitors. Mutat Res 821, 111695.
(8) Rose, M., Burgess, J. T., O'Byrne, K., Richard, D. J., and Bolderson, E. (2020). PARP Inhibitors: Clinical Relevance, Mechanisms of Action and Tumor Resistance. Front Cell Dev Biol 8, 564601.
(9) Xu, Z., Vandenberg, C. J., Lieschke, E., Di Rago, L., Scott, C. L., and Majewski, I. J. (2021). CHK2 Inhibition Provides a Strategy to Suppress Hematologic Toxicity from PARP Inhibitors. Mol Cancer Res 19, 1350-1360.
(10) Zatreanu, D., Robinson, H. M. R., Alkhatib, O., Boursier, M., Finch, H., Geo, L., Grande, D., Grinkevich, V., Heald, R. A., Langdon, S., et al. (2021). Poltheta inhibitors elicit BRCA-gene synthetic lethality and target PARP inhibitor resistance. Nature communications 12, 3636.
(11) Zhou, J., Gelot, C., Pantelidou, C., Li, A., Yucel, H., Davis, R. E., Farkkila, A., Kochupurakkal, B., Syed, A., Shapiro, G. I., et al. (2021). A first-in-class Polymerase Theta Inhibitor selectively targets Homologous-Recombination-Deficient Tumors. Nat Cancer 2, 598-610.

What is claimed is:

1. A method for the treatment of a cancer, which comprises administering to a subject in need of such treatment:
    a) a pharmaceutically effective amount of a compound that increases the amount of NAD$^+$ in the subject's cancer cells, and
    b) a pharmaceutically effective amount of a PARG inhibitor and optionally one or more PARP inhibitors, wherein the compound that increases the amount of NAD$^+$ comprises dihydronicotinamide riboside (NRH), the PARG inhibitor comprises (E)-1-(((p-Tolylthio)imino)methyl) naphthalen-2-ol, and the cancer is a glioma.

2. The method of claim 1, wherein the compounds administered in a) and b) are administered in any order or simultaneously.

3. The method of claim 1, wherein the PARP inhibitor comprises one or more of Olaparib, Rucaparib, Niraparib, Talazoparib, or Veliparib.

4. The method of claim 1, wherein the cancer cells contain a functional MSH6 protein.

5. The method of claim 1, which further comprises determining whether the cancer to be treated contains a functional MSH6 protein prior to administering the compounds in a) and b).

* * * * *